(12) United States Patent
Hashimoto

(10) Patent No.: US 11,982,542 B2
(45) Date of Patent: May 14, 2024

(54) NUMBER OF STEPS MEASURING DEVICE, METHOD, AND PROGRAM

(71) Applicant: Nippon Telegraph and Telephone Corporation, Tokyo (JP)

(72) Inventor: Yuki Hashimoto, Tokyo (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 403 days.

(21) Appl. No.: 17/293,756

(22) PCT Filed: Jan. 7, 2020

(86) PCT No.: PCT/JP2020/000148
§ 371 (c)(1),
(2) Date: May 13, 2021

(87) PCT Pub. No.: WO2020/149171
PCT Pub. Date: Jul. 23, 2020

(65) Prior Publication Data
US 2021/0404842 A1    Dec. 30, 2021

(30) Foreign Application Priority Data
Jan. 15, 2019    (JP) ................................ 2019-004157

(51) Int. Cl.
*G01C 22/00* (2006.01)
*A63B 24/00* (2006.01)
*G01P 15/18* (2013.01)

(52) U.S. Cl.
CPC ........ *G01C 22/006* (2013.01); *A63B 24/0062* (2013.01); *G01P 15/18* (2013.01);
(Continued)

(58) Field of Classification Search
CPC .............. G01C 22/006; A63B 24/0062; A63B 2220/17; A63B 2220/40; A63B 2220/803; A63B 2220/836; G01P 15/18
(Continued)

(56) References Cited

U.S. PATENT DOCUMENTS 8,280,678 B2 * 10/2012 Lee ....................... G01C 22/006
701/527
9,200,923 B2 * 12/2015 Lammel ................. G06V 40/25
(Continued)

FOREIGN PATENT DOCUMENTS

| JP | 2010119500 A | 6/2010 |
| JP | 2017038631 A | 2/2017 |

(Continued)

OTHER PUBLICATIONS

Hokuriku Electric Industry Co., Ltd., "3-axis accelerometer application note Piezoresistive 3-axis accelerometer HAAM-326B Pedometer," First Edition, Feb. 2007, pp. 1-6. As discussed in the specification.

*Primary Examiner* — Max H Noori
(74) *Attorney, Agent, or Firm* — Slater Matsil, LLP

(57) ABSTRACT

A first calculation unit synthesizes respective measured values of acceleration of an X-axis, a Y-axis and a Z-axis measured by a measurement unit and calculates the synthesized acceleration. A second calculation unit calculates acceleration in a body axis direction (vertical direction) of a wearer wearing the measurement unit from the respective measured values of acceleration of the X-axis, the Y-axis and the Z-axis. The third calculation unit calculates amplitude of a time variation of acceleration in the body axis direction calculated by the second calculation unit. A reference setting unit sets a reference time for determining one step based on the amplitude calculated by the third calculation unit. A walking detection unit detects one-step walking motion of
(Continued)

the wearer, a one-step time of which falls within a range of the reference time based on the synthesized acceleration.

9 Claims, 4 Drawing Sheets

(52) U.S. Cl.
CPC ....... *A63B 2220/17* (2013.01); *A63B 2220/40* (2013.01); *A63B 2220/803* (2013.01); *A63B 2220/836* (2013.01)

(58) Field of Classification Search
USPC ....................................................... 73/865.4
See application file for complete search history.

(56) References Cited

U.S. PATENT DOCUMENTS

| | | | |
|---|---|---|---|
| 10,030,993 B2* | 7/2018 | Barfield | ................... G01C 5/06 |
| 10,564,178 B2* | 2/2020 | Poduri | ................... G01P 21/00 |
| 10,820,836 B2* | 11/2020 | Winter | ................... G01P 13/00 |
| 11,698,385 B2* | 7/2023 | Kim | ................... G01P 15/18 |
| | | | 73/379.01 |
| 2007/0143068 A1* | 6/2007 | Pasolini | ................ G01C 22/006 |
| | | | 702/160 |
| 2010/0121605 A1* | 5/2010 | Ohta | ................... G01C 22/006 |
| | | | 702/160 |
| 2011/0133682 A1* | 6/2011 | Egger | ....................... H02P 8/38 |
| | | | 318/685 |
| 2011/0196264 A1 | 8/2011 | Asada | |
| 2014/0188431 A1* | 7/2014 | Barfield | ................... G01C 5/06 |
| | | | 702/160 |
| 2020/0158533 A1* | 5/2020 | Sekiguchi | ........... G01C 21/206 |

FOREIGN PATENT DOCUMENTS

| | | |
|---|---|---|
| JP | 2018079102 A | 5/2018 |
| WO | 2018089916 A1 | 5/2018 |

\* cited by examiner

NUMBER OF STEPS MEASURING DEVICE, METHOD, AND PROGRAM

CROSS-REFERENCE TO RELATED APPLICATIONS

This application is a national phase entry of PCT Application No. PCT/JP2020/000148, filed on Jan. 7, 2020, which claims priority to Japanese Application No. 2019-004157, filed on Jan. 15, 2019 which applications are hereby incorporated herein by reference.

TECHNICAL FIELD

The present invention relates to a step-counting device and method, and program.

BACKGROUND

In recent years, because of increasing health-consciousness along with an aging population worldwide, a growing number of people have been reviewing and improving their lifestyles through measurement and monitoring of their own biological information in daily life. A pedometer is one of such biological information measurement devices, detects walking or running action of a wearer of the pedometer and measures the number of steps by an acceleration sensor.

During walking or running of common humans, grounding and lifting of the feet take place periodically, and peaks of acceleration periodically appear in a body axis direction (direction of gravity) of pedestrians. Pedometers using an acceleration sensor measure the number of steps by detecting such acceleration peaks one by one for each walking motion (see Patent Literature 1).

CITATION LIST

Patent Literature

Patent Literature 1: Japanese Patent Application Laid-Open No. 2017-038631

Non-Patent Literature

Non-Patent Literature 1: "Three-Axis Acceleration Sensor Application Note Piezo Resistance Type Three-Axis Acceleration Sensor HAAM-326B Pedometer Part," Hokuriku Electric Industry Co., Ltd., first edition, 2007.

SUMMARY

Technical Problem

However, a plurality of peaks may be generated in measured acceleration during one-step motion, and the aforementioned technique accordingly involves a problem of erroneously detecting each peak generated in one step as walking motion.

Embodiments of the present invention has been made to solve the above problem and it is an object of embodiments of the present invention to reduce erroneous detections of walking motion.

Means for Solving the Problem

A step-counting device according to embodiments of the present invention includes a first calculation unit configured to synthesize respective measured values of acceleration of a plurality of measuring axes measured by a measurement unit that measures acceleration of the plurality of measuring axes and calculate the synthesized acceleration, a second calculation unit configured to calculate acceleration in a body axis direction of a wearer wearing the measurement unit from the respective measured values of acceleration of the plurality of measuring axes, a third calculation unit configured to calculate amplitude of a time variation of the acceleration calculated by the second calculation unit, a reference setting unit configured to set a reference time for determining one step based on the amplitude, a walking detection unit configured to detect walking motion by the wearer based on the synthesized acceleration, a one-step time of the wearer falling within a range of the reference time in the walking motion, and a fourth calculation unit configured to calculate the number of steps of the walking motion detected by the walking detection unit.

In one configuration example of the step-counting device, the step-counting device further includes a fifth calculation unit configured to calculate the time required for one step of the walking motion detected by the walking detection unit.

In one configuration example of the step-counting device, the second calculation unit includes a low-pass filter configured to extract a gravity acceleration component from the respective measured values of acceleration of the plurality of measuring axes and calculates acceleration in the body axis direction of the wearer by subtracting the gravity acceleration component from the respective measured values of acceleration of the plurality of measuring axes.

In one configuration example of the step-counting device, the second calculation unit calculates a deviation between the body axis direction of the wearer and a coordinate axis of the measurement unit, corrects and calculates acceleration in the body axis direction of the wearer according to the calculated deviation.

A step-counting method according to embodiments of the present invention includes a first step of synthesizing respective measured values of acceleration of a plurality of measuring axes measured by a measurement unit that measures acceleration of the plurality of measuring axes and calculating the synthesized acceleration, a second step of calculating acceleration in a body axis direction of a wearer wearing the measurement unit from the respective measured values of acceleration of the plurality of measuring axes, a third step of calculating amplitude of a time variation of the acceleration calculated in the second step, a fourth step of setting a reference time for determining one step based on the amplitude, a fifth step of detecting walking motion by the wearer based on the synthesized acceleration, a one-step time of the wearer falling within a range of the reference time in the walking motion, and a sixth step of calculating the number of steps of the walking motion detected in the fifth step.

In one configuration example of the step-counting method, the step-counting method further includes a seventh step of calculating a time required for one step of the walking motion detected in the fifth step.

In one configuration example of the step-counting method, in the second step, a gravity acceleration component is extracted from the respective measured values of acceleration of the plurality of measuring axes and acceleration in the body axis direction of the wearer is calculated by subtracting the gravity acceleration component from the respective measured values of acceleration of the plurality of measuring axes.

In one configuration example of the step-counting method, in the second step, a deviation between the body axis direction of the wearer and a coordinate axis of the measurement unit is calculated, and acceleration in the body axis direction of the wearer is corrected and calculated according to the calculated deviation.

A program according to embodiments of the present invention is a program for causing a computer to execute each step in the step-counting method.

Effects of Embodiments of the Invention

As described above, according to embodiments of the present invention, a reference time for determining one step based on amplitude of a time variation in acceleration in the body axis direction is set, and it is therefore possible to reduce erroneous detections of walking motion.

DETAILED DESCRIPTION OF ILLUSTRATIVE EMBODIMENTS

Figure 1:
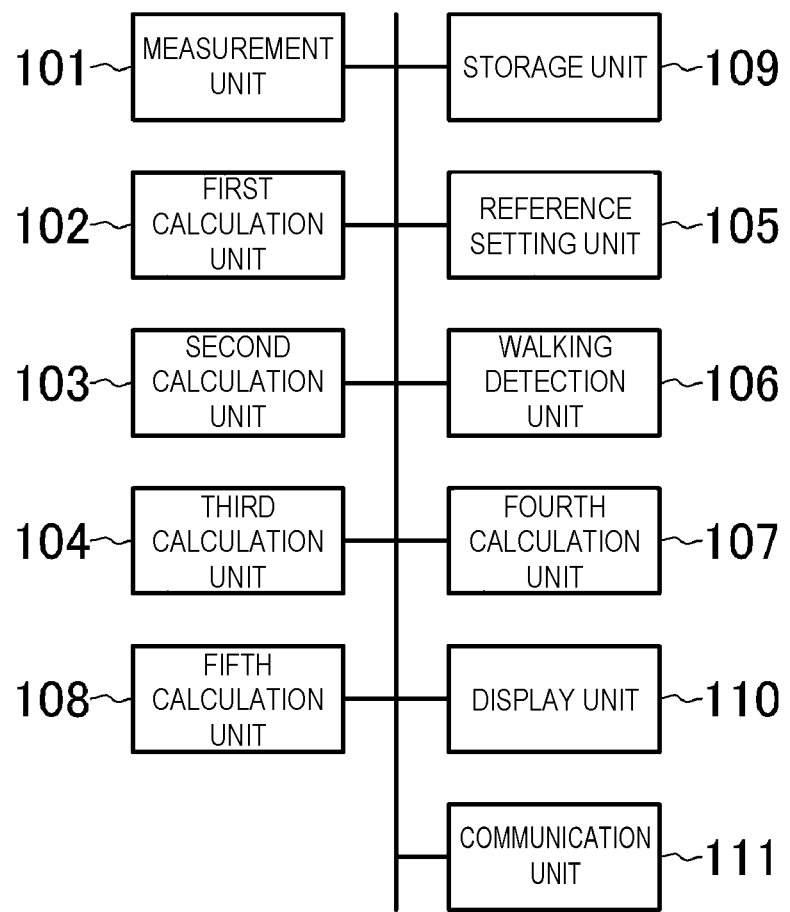
FIG. 1 is a configuration diagram illustrating a configuration of a step-counting device according to an embodiment of the present invention.

Hereinafter, a step-counting device according to an embodiment of the present invention will be described with reference to FIG. 1. This step-counting device includes a measurement unit 101, a first calculation unit 102, a second calculation unit 103, a third calculation unit 104, a reference setting unit 105, a walking detection unit 106 and a fourth calculation unit 107. The walking measurement device according to the embodiment includes a fifth calculation unit 108, a display unit 110 and a communication unit 111.

The measurement unit 101 is composed of an acceleration sensor including a plurality of measuring axes, and worn by a person to be measured (wearer) to measure acceleration. The measurement unit 101 includes an analog/digital converter configured to convert an analog signal acquired by the acceleration sensor to a digital signal at a sampling rate of, for example, 25 Hz and output the digital signal as a measured value of acceleration on each axis. For example, the measurement unit 101 periodically measures acceleration in three directions of X-axis, Y-axis and Z-axis, which are orthogonal to each other, and thereby obtains a time sequence of measured values of acceleration. The measured values of acceleration measured by the measurement unit 101 are stored, for example, in a storage unit 109. For example, the storage unit 109 is composed of a non-volatile memory represented by a flash memory, or a volatile memory such as a DRAM (dynamic random access memory).

The first calculation unit 102 synthesizes the respective measured values of acceleration of the X-axis, Y-axis and Z-axis measured by the measurement unit 101 and calculates synthesized acceleration. The first calculation unit 102 calculates the synthesized acceleration from the measured values of acceleration stored in the storage unit 109. For example, the first calculation unit 102 calculates the synthesized acceleration based on an nth (n≥1) acceleration component ($a_X[n]$, $a_Y[n]$, $a_Z[n]$) measured by the measurement unit 101 from the start of measurement based on Expression (1).

Here, X, Y and Z represent measuring axes of the acceleration sensor of the measurement unit 101 in an orthogonal coordinate system and $\alpha_X$, $\alpha_Y$ and $\alpha_Z$ represent the respective components of acceleration in the present coordinate system. In the embodiment, it is assumed that the measurement unit 101 is mounted so that the X and Y axes face the horizontal direction and the Z axis faces the body axis direction of the wearer.

Math. 1

$$\text{Synthesized acceleration } |\vec{a}[n]| = \sqrt{(a_X[n])^2 + (a_Y[n])^2 + (a_Z[n])^2} \quad (1)$$

where $\vec{a}[n] = (a_X[n], a_Y[n], a_Z[n])$

The second calculation unit 103 calculates acceleration in the body axis direction (vertical direction) of the wearer wearing the measurement unit 101 from the respective measured values of acceleration of the X-axis, the Y-axis and the Z-axis. The second calculation unit 103 calculates acceleration in the body axis direction from the measured values of acceleration stored in the storage unit 109.

In the embodiment, the second calculation unit 103 extracts the gravity acceleration component from the nth (n≥1) acceleration component ($a_X[n]$, $a_Y[n]$, $a_Z[n]$) measured by the measurement unit 101 from the start of measurement. Furthermore, the second calculation unit 103 calculates a deviation (angle) between the body axis direction (gravity direction) and the coordinate axis (Z-axis) of the measurement unit 101, corrects and calculates acceleration in the body axis direction (vertical direction) according to the calculated deviation.

More specifically, the second calculation unit 103 first extracts the gravity component by removing a high-frequency component from the acceleration component measured by the measurement unit 101 using a low-pass filter. A low-pass filter shown in Expression (2) is used as an example in the embodiment.

Math. 2

$$\text{Gravity component } \vec{a_L}[n] = \vec{a_L}[n-1] \times \alpha + \vec{a}[n] \times (1-\alpha) \quad (2)$$

In Expression (2), $\alpha$ is an arbitrary filter coefficient and takes a value $0 < \alpha < 1$. Setting $\alpha$ to a value close to 1 broadens the frequency domain to be removed, and can thereby remove a drastic acceleration variation. The filter coefficient $\alpha = 0.9$ is set in the embodiment. Note that the calculation using Expression (2) is merely an example, and any calculation can be used if such a calculation allows the gravity component to be extracted.

Next, as shown in Expression (3), a non-gravity component is calculated by subtracting the gravity component obtained by Expression (2) from the acceleration component measured by the measurement unit 101.

Math. 3

$$\text{Non-gravity component } \vec{a_H}[n] = \vec{a}[n] - \vec{a_L}[n] \quad (3)$$

Next, a process of correcting a deviation from the gravity acceleration direction of the Z-axis of the measurement unit 101 is performed to calculate acceleration in the body axis direction. More specifically, an angle θ formed by a vector consisting of the gravity component and the corrected vector (g is gravity acceleration) is calculated using Expression (4). A unit vector perpendicular to both of the vectors is calculated using Expression (5).

Math. 4

$$\theta = \cos^{-1}\left(\frac{\vec{G} \cdot \vec{G^*}}{\vec{G} \times \vec{G^*}}\right) \quad (4)$$

$$\vec{n} = \frac{\vec{G} \times \vec{G^*}}{|\vec{G} \times \vec{G^*}|} \quad (5)$$

Vector consisting of gravity component
$\vec{G} = (\alpha_{LX}(n), \alpha_{LY}(n), \alpha_{LZ}(n))$ Corrected vector $\vec{G^*} = (0, 0, g)$, where g is gravity acceleration.

Next, the non-gravity component in the corrected body axis direction (z direction) is calculated using Expression (6) shown below and the calculated non-gravity component is assumed to be the acceleration in the body axis direction.

Math. 5

Non-gravity component in body-axis direction $\alpha_{HZ}^*$
$[n] = \{n_Z n_X(1-\cos\theta) + n_Y \sin\theta\} \times \alpha_{HX}[n] + \{n_Y n_Z (1-\cos\theta) - n_X \sin\theta\} \times \alpha_{HY}[n] + \{n_Z^2(1-\cos\theta) + \cos\theta\} \times \alpha_{HZ}[n]$ (6)

where $\vec{n} = (n_x, n_y, n_z)|$,

The third calculation unit 104 calculates amplitude of a time variation of the acceleration ($\alpha^*_{HZ}[n]$) in the body axis direction calculated by the second calculation unit 103. The reference setting unit 105 sets a reference time for determining one step based on the amplitude calculated by the third calculation unit 104.

The walking detection unit 106 detects a one-step walking (or running) motion by the wearer, the one-step time of which falls within a range of the reference time, based on the synthesized acceleration. In the embodiment, the walking detection unit 106 determines one step when the synthesized acceleration first takes a value lower than a first threshold (e.g., 0.9 [m/s²]) and then takes a value higher than a second threshold (e.g., 1.1 [m/s²]) (see Non-Patent Literature 1). Next, when an elapsed time (one-step time) at a point in time at which the second threshold is exceeded this time after exceeding the second threshold last time falls within a range of the reference time set by the reference setting unit 105, this one step is detected as a walking (or running) motion.

Figure 3:
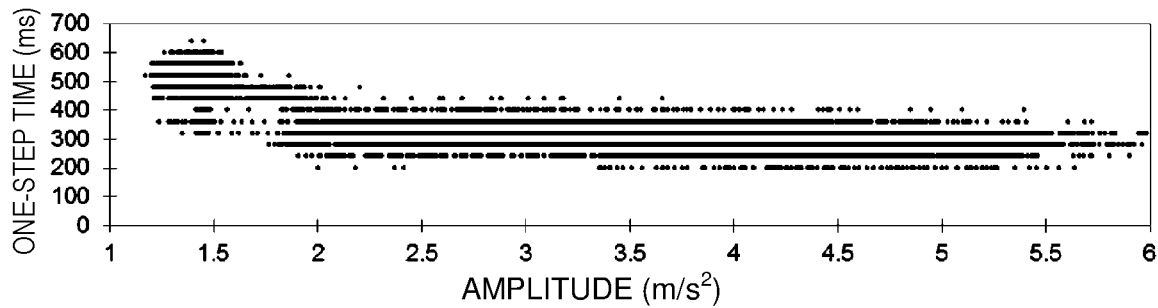
FIG. 3 is a characteristic diagram illustrating a relationship between measured amplitude of acceleration in the body axis direction and a one-step time.

The detection of the aforementioned one-step walking (or running) motion will be described more specifically. FIG. 3 illustrates a relationship between the amplitude of acceleration ($\alpha^*_{HZ}[n]$) in the measured body axis direction and the one-step time. As shown in FIG. 3, as the amplitude of body axis direction acceleration increases, an upper limit or a lower limit of the one-step time tends to decrease, and when the amplitude of body axis direction acceleration grows to a certain degree, an upper limit or a lower limit of the one-step time tends to be substantially unchanged. Therefore, by calculating the amplitude of body axis direction acceleration per step, it is possible to set an effective range of the one-step time.

The reference setting unit 105 according to the embodiment sets a reference time t of the one-step time according to the amplitude of the body axis direction acceleration ($\alpha^*_{HZ}[n]$) as shown below, as an example.

280 [ms]≤t≤720 [ms] (amplitude<1.7)

160 [ms]≤t≤560 [ms] (1.7≤amplitude<2.4)

160 [ms]≤t≤480 [ms] (2.4≤amplitude<3.8)

160 [ms]≤t≤420 [ms] (3.8≤amplitude)

For example, when the amplitude calculated by the third calculation unit 104 is smaller than 1.7 (m/s), the reference setting unit 105 sets the reference time t to 280 [ms] 720 [ms]. In this case, when the elapsed time (one-step time) is 280 [ms] or more and 720 [ms] or less, if the synthesized acceleration takes a value lower than the first threshold and then takes a value higher than the second threshold, the walking detection unit 106 detects it as one-step walking (walking motion). In this way, the fourth calculation unit 107 calculates the number of steps by the one-step walking (or running) motion detected by the walking detection unit 106. The fifth calculation unit 108 calculates a time (one-step time) required for the detected one-step walking motion.

The step-counting device according to the embodiment displays the number of steps calculated by the fourth calculation unit 107 and the one-step time calculated by the fifth calculation unit 108 on the display unit 110. For example, the display unit no can be composed of a display such as a liquid crystal display, an organic EL (electroluminescence) display or a plasma display.

In the step-counting device according to the embodiment, the communication unit 111 transmits the number of steps calculated by the fourth calculation unit 107 and the one-step time calculated by the fifth calculation unit 108 to an external device wirelessly such as BLE (Bluetooth low energy) or through wired communication such as Ethernet (registered trademark) via a predetermined network. Examples of the external device include smartphone, computer or smartwatch. Note that either one or both of the display unit no and the communication unit 111 may be provided on the step-counting device.

Figure 2:
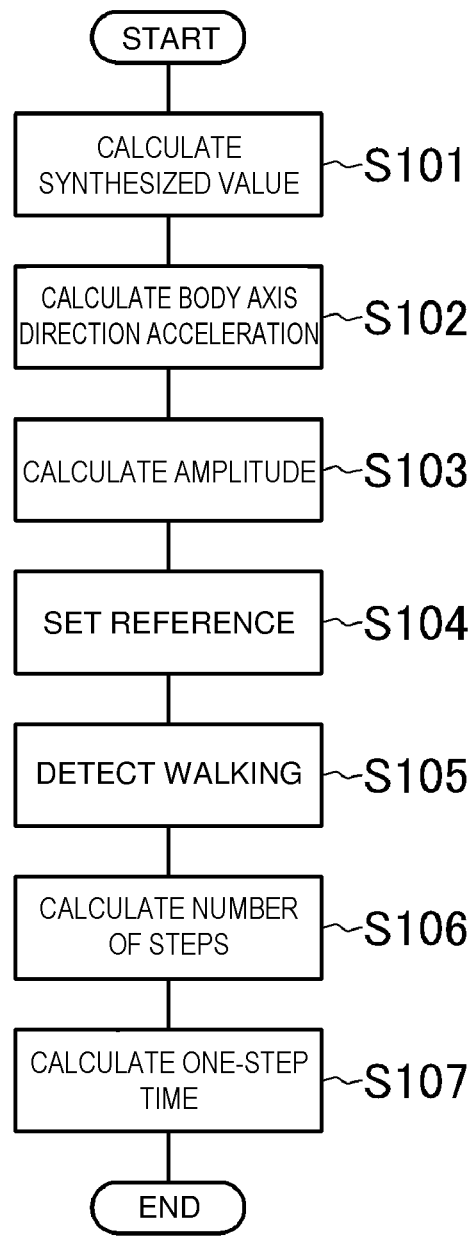
FIG. 2 is a flowchart illustrating step-counting according to the embodiment of the present invention.

Next, the step-counting method according to the embodiment of the present invention will be described with reference to FIG. 2.

First, in a first step S101, the first calculation unit 102 synthesizes respective measured values of acceleration of the plurality of measuring axes measured by the measurement unit 101 and calculates synthesized acceleration. Next, in a second step S102, the second calculation unit 103 calculates acceleration in the body axis direction of the wearer wearing the measurement unit 101 from the respective measured values of acceleration of the plurality of measuring axes. For example, acceleration in the body axis direction of the wearer is calculated by extracting the gravity acceleration component from the respective measured values of acceleration of the plurality of measuring axes and subtracting the gravity acceleration component from the respective measured values of acceleration of the plurality of measuring axes.

Next, in a third step S103, the third calculation unit 104 calculates amplitude of a time variation of acceleration in the calculated body axis direction. Next, in a fourth step S104, the reference setting unit 105 sets a reference time for determining one step based on the calculated amplitude. Next, in a fifth step S105, the walking detection unit 106 detects walking motion by the wearer, in which a one-step time of the wearer falls within a range of the reference time, based on the calculated synthesized acceleration. Next, in a sixth step S106, the fourth calculation unit 107 calculates the number of steps by the detected walking motion. In a seventh step S107, the fifth calculation unit 108 calculates a time required for one step of the detected walking motion.

Figure 4:
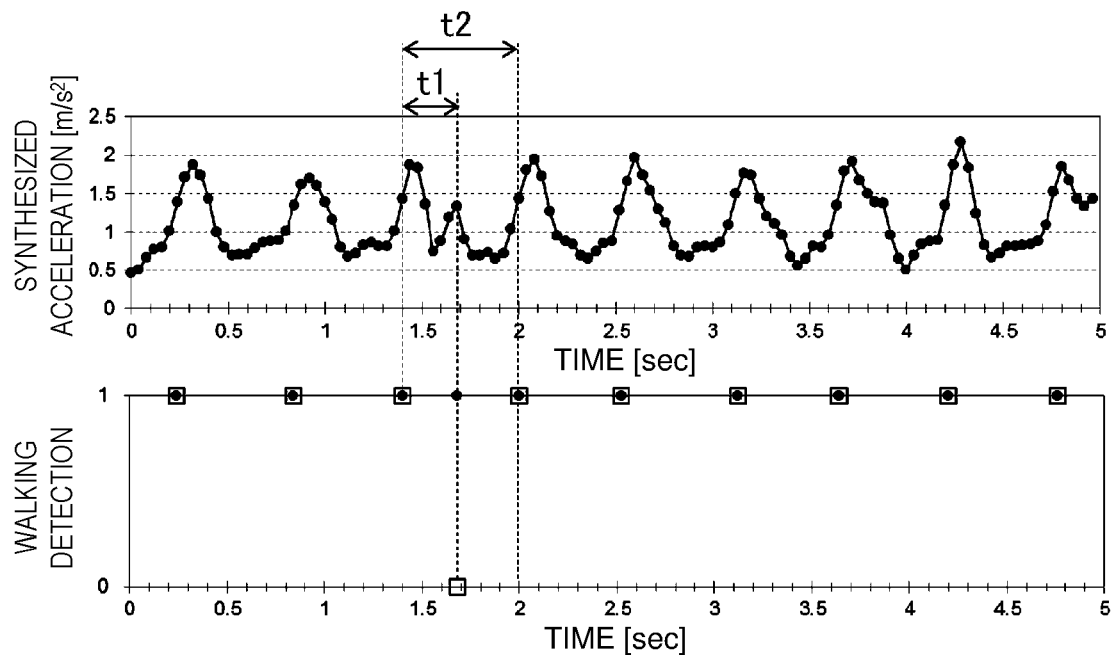
FIG. 4 is a diagram illustrating a walking detection result by the step-counting device according to the embodiment.

FIG. 4 illustrates walking detection results in the embodiment. In FIG. 4, black circles represent walking detection results according to the prior art and white rectangles represent walking detection results in the embodiment. In FIG. 4, t1 is outside the range of reference time and t2 is within the range of reference time. The prior art detects walking motion when a threshold is exceeded in the vicinity of time 1.4 s, and then erroneously detects walking motion also when a threshold is exceeded in the vicinity of 1.7 s. On the other hand, the embodiment does not count as walking based on the elapsed time t1 from the last detection when the threshold is exceeded in the vicinity of 1.7 s and detects as walking motion when a new threshold is exceeded after t2 elapses. Thus, it has been confirmed that embodiments of the present invention can reduce erroneous detection of walking motion.

Figure 5:
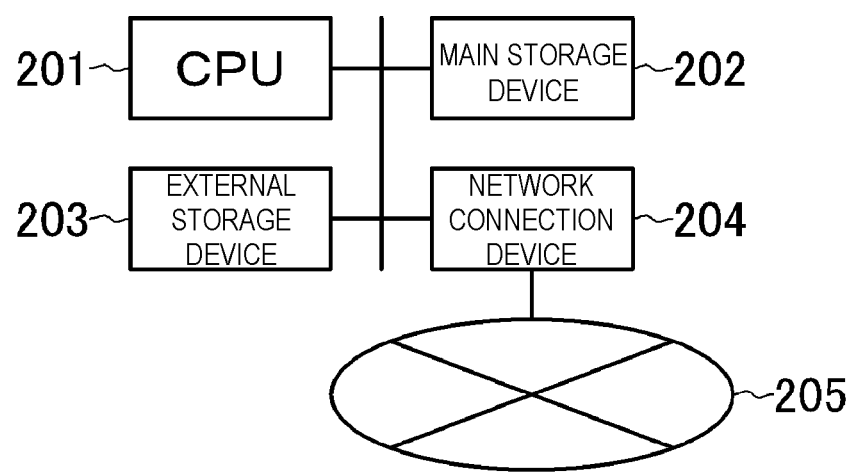
FIG. 5 is a configuration diagram illustrating a hardware configuration of the step-counting device according to embodiments of the present invention.

Note that the step-counting device according to the embodiment may be a computer device including a CPU (central processing unit) 201, a main storage device 202, an external storage device 203 and a network connection device 204 or the like as shown in FIG. 5 and the aforementioned respective functions (scheduling method) may be implemented by the CPU 201 operating (executing the program) according to a program developed in the main storage device 202. The above program is a program for the computer to execute the step-counting method shown in the aforementioned embodiment. The network connection device 204 is connected to the network 205. The respective functions may also be distributed among a plurality of computer devices.

The step-counting device in the aforementioned embodiment can also be composed of a programmable logic device (PLD) such as an FPGA (field-programmable gate array). For example, a circuit including the storage unit, the first calculation unit, the second calculation unit, the third calculation unit, the reference setting unit, the walking detection unit, the fourth calculation unit and the fifth calculation unit as logic elements of the FPGA can be made to function as the step-counting device. The first calculation circuit, the second calculation circuit, the third calculation circuit, the reference setting circuit, the walking detection circuit, the fourth calculation circuit and the fifth calculation circuit are each connected to a predetermined writing device to write the FPGA.

As described so far, according to embodiments of the present invention, since a reference time for determining one step is set based on the amplitude of a time variation of acceleration in the body axis direction, it is possible to reduce erroneous detections of walking motion.

Note that the present invention is not limited to the embodiment described so far, but it is obvious that many modifications and combinations can be made by those possessing ordinary knowledge in this field within the technical thought of the present invention.

REFERENCE SIGNS LIST 101 measurement unit
102 first calculation unit
103 second calculation unit
104 third calculation unit
105 reference setting unit
106 walking detection unit
107 fourth calculation unit
108 fifth calculation unit
109 storage unit
110 display unit
111 communication unit.

The invention claimed is:

1. A step-counting device comprising:
a first calculator configured to synthesize respective measured values of acceleration of a plurality of measuring axes measured by a measurement device, the measurement device being configured to measure acceleration of the plurality of measuring axes and calculate synthesized acceleration;
a second calculator configured to:
calculate a deviation between a body axis direction of a wearer and a coordinate axis of the measurement device; and
calculate acceleration in the body axis direction of the wearer wearing the measurement device according to the respective measured values of acceleration of the plurality of measuring axes and the deviation between the body axis direction of the wearer and the coordinate axis of the measurement device;
a third calculator configured to calculate amplitude of a time variation of the acceleration calculated by the second calculator;
a reference setting unit configured to set a reference time for determining one step based on the amplitude;
a walking detector configured to detect walking motion by the wearer based on the synthesized acceleration, a one-step time of the wearer falling within a range of the reference time in the walking motion; and
a fourth calculator configured to calculate a number of steps of the walking motion detected by the walking detector.

2. The step-counting device according to claim 1, further comprising a fifth calculator configured to calculate the one-step time corresponding to one step of the walking motion.

3. The step-counting device according to claim 1, wherein the second calculator comprises a low-pass filter configured to extract a gravity acceleration component from the respective measured values of acceleration of the plurality of measuring axes, wherein calculating the acceleration in the body axis direction of the wearer comprises subtracting the gravity acceleration component from the respective measured values of acceleration of the plurality of measuring axes.

4. A step-counting method comprising:
a first step of synthesizing respective measured values of acceleration of a plurality of measuring axes measured by a measurement device that measures acceleration of the plurality of measuring axes and calculates synthesized acceleration;

a second step of:
: calculating a deviation between a body axis direction of a wearer and a coordinate axis of the measurement device; and
: calculating acceleration in the body axis direction of the wearer wearing the measurement device according to the respective measured values of acceleration of the plurality of measuring axes and the deviation between the body axis direction of the wearer and the coordinate axis of the measurement device;

a third step of calculating amplitude of a time variation of the acceleration calculated in the second step;

a fourth step of setting a reference time for determining one step based on the amplitude;

a fifth step of detecting walking motion by the wearer based on the synthesized acceleration, a one-step time of the wearer falling within a range of the reference time in the walking motion; and a sixth step of calculating a number of steps of the walking motion detected in the fifth step.

5. The step-counting method according to claim 4, further comprising a seventh step of calculating a time corresponding to one step of the walking motion detected in the fifth step.

6. The step-counting method according to claim 4, wherein in the second step, a gravity acceleration component is extracted from the respective measured values of acceleration of the plurality of measuring axes and acceleration in the body axis direction of the wearer is calculated by subtracting the gravity acceleration component from the respective measured values of acceleration of the plurality of measuring axes.

7. A non-transitory memory storing a program, that when executed by a computer, causes the computer to perform each step in a step-counting method, wherein the step-counting method comprises:

a first step of synthesizing respective measured values of acceleration of a plurality of measuring axes measured by a measurement device that measures acceleration of the plurality of measuring axes and calculating synthesized acceleration;

a second step of:
: calculating a deviation between a body axis direction of a wearer and a coordinate axis of the measurement device; and
: calculating acceleration in the body axis direction of the wearer wearing the measurement device according to the respective measured values of acceleration of the plurality of measuring axes and the deviation between the body axis direction of the wearer and the coordinate axis of the measurement device;

a third step of calculating amplitude of a time variation of the acceleration calculated in the second step;

a fourth step of setting a reference time for determining one step based on the amplitude;

a fifth step of detecting walking motion by the wearer based on the synthesized acceleration, a one-step time of the wearer falling within a range of the reference time in the walking motion; and a sixth step of calculating a number of steps of the walking motion detected in the fifth step.

8. The non-transitory memory according to claim 7, wherein the step-counting method further comprises a seventh step of calculating a time corresponding to one step of the walking motion detected in the fifth step.

9. The non-transitory memory according to claim 7, wherein in the second step, a gravity acceleration component is extracted from the respective measured values of acceleration of the plurality of measuring axes and acceleration in the body axis direction of the wearer is calculated by subtracting the gravity acceleration component from the respective measured values of acceleration of the plurality of measuring axes.

\* \* \* \* \*